United States Patent
Sato

[11] Patent Number: 5,929,235
[45] Date of Patent: Jul. 27, 1999

[54] AROMATIC TERTIARY AMINE COMPOUND HAVING BENZAZEPINE STRUCTURES

[75] Inventor: Tadahisa Sato, Kanagawa, Japan

[73] Assignee: Fuji Photo Film Co., Ltd., Kanagawa, Japan

[21] Appl. No.: 08/914,248

[22] Filed: Aug. 19, 1997

[30] Foreign Application Priority Data

Aug. 20, 1996 [JP] Japan ................................ 8-235787

[51] Int. Cl.⁶ .................... C07D 223/18; C07D 223/26
[52] U.S. Cl. .................. 540/576; 540/588; 540/591; 540/592
[58] Field of Search .................. 540/576, 591, 540/592, 588

[56] References Cited

U.S. PATENT DOCUMENTS 5,629,421  5/1997  Takesue ................................. 540/591

FOREIGN PATENT DOCUMENTS 63-235946  9/1988  Japan .

Primary Examiner—Evelyn Mei Huang
Attorney, Agent, or Firm—Sughrue, Mion, Zinn, Macpeak & Seas, PLLC

[57] ABSTRACT

An aromatic tertiary amine compound of formula (I):

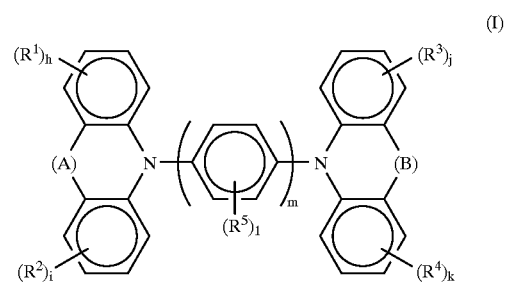

wherein (A) and (B) are each a substituted or unsubstituted vinylene or o-arylene group; $R^1$ to $R^4$ are each a halogen atom, or a substituted or unsubstituted alkyl, aryl, alkoxy, aryloxy, dialkylamino, N-alkyl-N-arylamino or diarylamino group; $R^5$ is a halogen atom, or a substituted or unsubstituted alkyl, alkoxy or dialkylamino group; h, i, j, k and l are each an integer of 0–4; and m is an integer of 1–6.

4 Claims, No Drawings

AROMATIC TERTIARY AMINE COMPOUND HAVING BENZAZEPINE STRUCTURES

FIELD OF THE INVENTION

The present invention relates to a benzazepine derivative. In particular, the invention concerns an aromatic tertiary amine compound having benzazepine skeletons in its molecular structure which is useful for an organic electroluminescent material, electrophotographic material or the like.

BACKGROUND OF THE INVENTION

VanSlyke, Tang and others have elucidated, e.g., in U.S. Pat. Nos. 4,539,507 and 4,720,432, and JP-A-05-234681 (The term "JP-A" as used herein means an "unexamined published Japanese patent application") that the use of aromatic tertiary amines having phenyl, phenylene or biphenylene groups in the hole injection-transport zone of an internal junction organic electroluminescence apparatus can elevate the light-output stability and lengthen the operational lifetime. For the purpose of further elevating the light-output stability, various modifications of aromatic tertiary amines used in the hole injection-transport zone have been tried by many investigators, and the results thereof have been applied for patents and published in academic journals. For instance, the modifications of biphenyl group-containing tertiary amines are disclosed, e.g., in *Japanese Journal of Applied Physics*, 27, L269 (1988), JP-A-59-194393, *Appl. Phys. Lett.*, 66, 2679 (1995), JP-A-05-234681, JP-A-07-331238, JP-A-08-48656 and WO 95/09147; and those of starburst type tertiary amines are disclosed, e.g., in *Appl. Phys. Lett.*, 65, 807 (1944) and JP-B-07-110940 (The term "JP-B" as used herein means an "examined Japanese patent publication").

Aromatic tertiary amines have been acquiring importance as an electrophotographic material also, and their utilization as a hole transporting material have been applied for patents. For instance, such amines are disclosed in JP-58-32372, JP-A-63-23594 and JP-A-01-142657. And effective use thereof is already made in midget plain-paper copying machines to contribute towards the popularization of low-priced copying machines.

As mentioned above, aromatic tertiary amines are of usefulness as an organic electroluminescent material and an electrophotographic material, but they are still inferior to inorganic materials in stabilities to heat and light. Therefore, improvements in their stabilities remain a weighty subject of research. More specifically, the problems confronting conventional aromatic tertiary amines as an organic electroluminescent material are as follows: Since the film of a conventional aromatic tertiary amine formed on an element by vacuum evaporation has insufficient stability, the properties thereof is changed by the crystallization occurring by lapse of time and being promoted by a rise in the element temperature due to the generation of heat during the operation to result in a lowering of the luminous efficiency, the appearance of a non-electroluminescent area called a dark spot and an increase in the number of dark spots, and further a rise in the voltage under constant-current operation. Thus, the element is ended up with a breakdown. This being the case, it has been desired to develop aromatic tertiary amines which can form stable films.

SUMMARY OF THE INVENTION

As a result of our intensive studies with the purpose of developing an aromatic tertiary amine which functions as hole transporting material and hardly undergoes various changes, including a physical change, an optical change and an electrochemical change, it has been found that a novel aromatic tertiary amine having benzazepine structures can answer our purpose, thereby achieving the present invention.

That is, the object of the present invention is attained with a novel aromatic tertiary amine compound represented by the following formula (I):

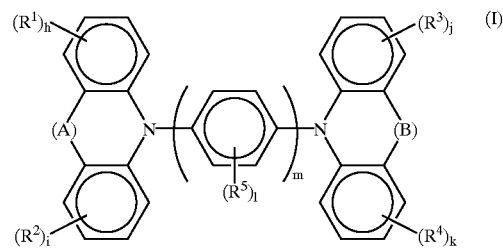

wherein (A) and (B) are each a substituted or unsubstituted vinylene or o-arylene group; $R^1$, $R^2$, $R^3$ and $R^4$ are each a halogen atom, or a substituted or unsubstituted alkyl, aryl, alkoxy, aryloxy, dialkylamino, N-alkyl-N-arylamino or diarylamino group; $R^5$ is a halogen atom, or a substituted or unsubstituted alkyl, alkoxy or dialkylamino group; h, i, j, k and l are each an integer of from 0 to 4; m is an integer of from 1 to 6; and wherein, when m is 2 or more, m sets of the substituents $(R^5)_l$ present on their respective benzene rings may be the same as or different from one another.

DETAILED DESCRIPTION OF THE INVENTION

The present compound represented by formula (I) is described below in detail.

(A) and (B) in formula (I) are each a substituted or unsubstituted vinylene or o-arylene group. Specific examples of such groups in the unsubstituted form are illustrated below:

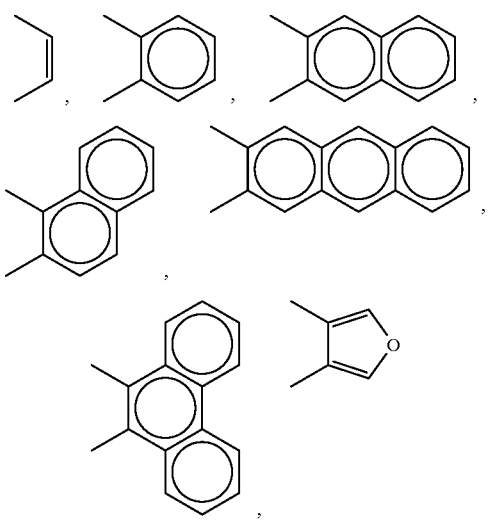

As for the groups preferred as (A) and (B), substituted or unsubstituted vinylene and o-phenylene groups are examples thereof.

More specifically, the compound preferred in the present invention has the following structural formula (II) or (III):

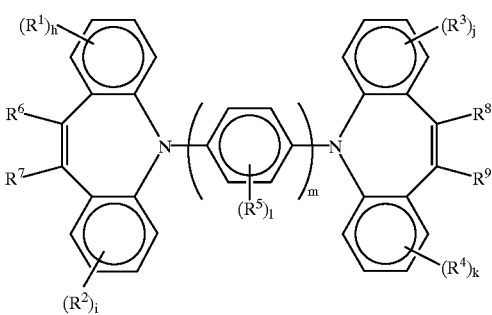

(II)

wherein $R^1$ to $R^4$, $R^5$, h to l, and m have the same meanings as those in formula (I), respectively; and $R^6$, $R^7$, $R^8$ and $R^9$ are each a hydrogen atom, a substituted or unsubstituted alkyl, aryl, alkoxy or alkoxycarbonyl group, or a cyano group;

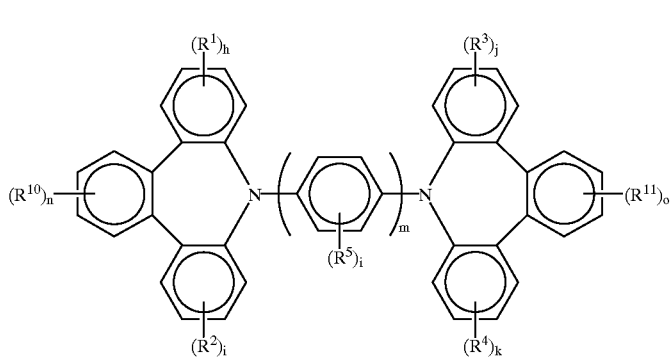

(III)

wherein $R^1$ to $R^4$, $R^5$, h to l and m have the same meanings as those in formula (I), respectively; $R^{10}$ and $R^{11}$ are each the same group as $R^1$, $R^2$, $R^3$ or $R^4$ represents; and n and o are each the same integer as h, i, j, k or l represents.

The substituents $R^1$ to $R^{11}$ and the subscripts h to o in formulae (I) to (III) are illustrated below in detail.

Each of the substituents $R^1$, $R^2$, $R^3$, $R^4$, $R^{10}$ and $R^{11}$ represents a halogen atom, or a substituted or unsubstituted alkyl, aryl, alkoxy, aryloxy, dialkylamino, N-alkyl-N-arylamino or diarylamino group. Specifically, the foregoing halogen atom is a fluorine, chlorine, bromine or iodine atom, and the foregoing unsubstituted group is an alkyl group having 1 to 20 carbon atoms, an aryl group having 6 to 36 carbon atoms, an alkoxy group having 1 to 20 carbon atoms, an aryloxy group having 6 to 36 carbon atoms, a dialkylamino group having 2 to 20 carbon atoms, an N-alkyl-N-arylamino group having 7 to 42 carbon atoms, or a diarylamino group having 12 to 48 carbon atoms.

More specifically, the unsubstituted groups recited above are an alkyl group such as-methyl, ethyl, isopropyl, n-butyl, t-butyl, n-dodecyl or cyclohexyl group, an aryl group such as phenyl, naphthyl, anthracenyl, phenanthrenyl, pyrenyl, naphthacenyl, pentacenyl or pentaphenyl group, an alkoxy group such as methoxy, ethoxy, isopropoxy, n-hexyloxy, cyclohexyloxy, octyloxy or dodecyloxy group, an aryloxy group such as phenoxy, naphthoxy, anthracenoxy or pentacenoxy group, a dialkylamino group such as dimethylamino, diethylamino, dibutylamino, dioctylamino or N-ethyl-N-butylamino group, an N-alkyl-N-arylamino group such as N-methyl-N-phenylamino, N-ethyl-N-phenylamino, N-isopropyl-N-(3-methylphenyl)amino, N-methyl-N-(1-naphthyl)amino or N-butyl-N-(1-naphthacenyl)amino group, and a diarylamino group such as diphenylamino, N-phenyl-N-(1-naphthyl)amino, N-(1-naphthyl)-N-(1-naphthyl)amino, N-phenyl-N-(1-anthracenyl)amino or N-(1-anthracenyl)-N-(1-phenanthrenyl) amino group.

In cases where the above-recited groups have substituent groups, examples of such substituent groups include a halogen atom, an alkyl group, an aryl group, a heterocyclic group, a cyano group, a hydroxyl group, a nitro group, a carboxyl group, a sulfo group, an amino group, an alkoxy group, an aryloxy group, an acylamino group, an alkylamino group, an anilino group, an ureido group, a sulfamoylamino group, an alkylthio group, an arylthio group, an alkoxycarbonylamino group, a sulfonamido group, a carbamoyl group, a sulfamoyl group, a sulfonyl group, an alkoxycarbonyl group, a heterocyclyloxy group, an azo group, an acyloxy group, a carbamoyloxy group, a silyloxy group, an aryloxycarbonylamino group, an imido group, a heterocyclythio group, a sulfinyl group, a phosphonyl group, an aryloxycarbonyl group, an acyl group, a silyl group and an azolyl group.

As for the substituents $R^1$ to $R^4$, $R^{10}$ and $R^{11}$ each, a halogen atom, an alkyl group, an alkoxy group, a dialkylamino group and a diarylamino group are favorable examples thereof. In particular, an alkyl group and a dialkylamino group are preferred over the others.

$R^5$ represents a halogen atom, or a substituted or unsubstituted alkyl, alkoxy or dialkylamino group. Specific examples of these groups include the same ones as recited in the detailed description of the substituents $R^1$ to $R^4$, $R^{10}$ and $R^{11}$. More specifically, it is desirable for $R^5$ to be a halogen atom or an unsubstituted alkyl or alkoxy group, especially a fluorine atom, a chlorine atom, a methyl group or a methoxy group.

Each of the substituents $R^6$, $R^7$, $R^8$ and $R^9$ represents a hydrogen atom, a halogen atom, a substituted or unsubstituted alkyl, aryl, alkoxy or alkoxycarbonyl group, or a cyano group. As for these groups except a hydrogen atom and a cyano group, the halogen atom is specifically a fluorine, chlorine, bromine or iodine atom, and the unsubstituted groups are specifically an alkyl group such as methyl, ethyl, butyl, t-butyl or n-octyl, an aryl group such as phenyl, 1-naphthyl, 2-naphthyl or 2-anthracenyl, an alkoxy group such as methoxy, ethoxy or n-butyloxy, and an alkoxycarbonyl group such as methoxycarbonyl, ethoxycarbonyl or octyloxycarbonyl. In cases where the above-cited groups have substituent groups, examples of such substituent groups include the substituent groups recited in the detailed description of $R^1$ to $R^4$, $R^{10}$ and $R^{11}$.

The group preferred as each of the substituents $R^6$ to $R^9$ is a hydrogen atom, an alkyl group or an aryl group, especially a hydrogen atom or an alkyl group.

Further, the subscripts h to o are described below in detail. The subscripts h, i, j, k, l, n and o are each an integer of from 0 to 4, preferably from 0 to 2, particularly preferably 0 or 1. The subscript m is an integer of from 1 to 6, preferably from 2 to 4, particularly preferably 2.

Specific examples of the present compound represented by formula (I) are illustrated below, but these examples are not to be considered as limiting the scope of the present invention in any way.

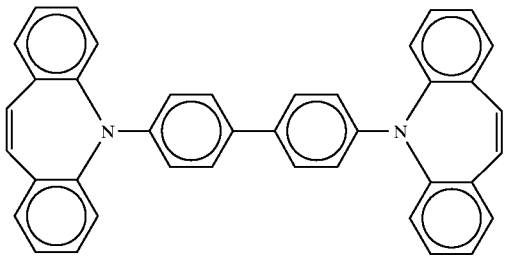

(1)

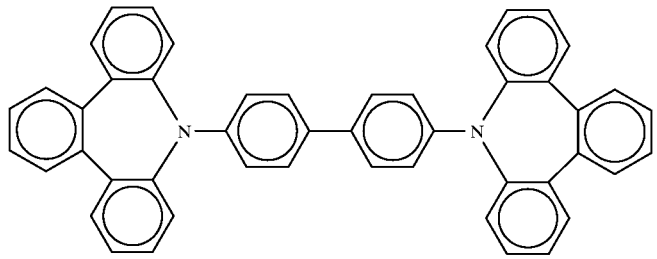

(2)

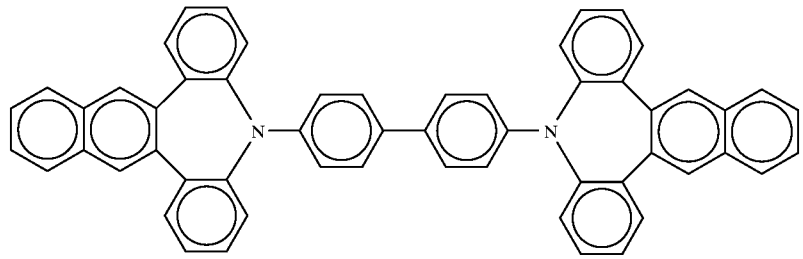

(3)

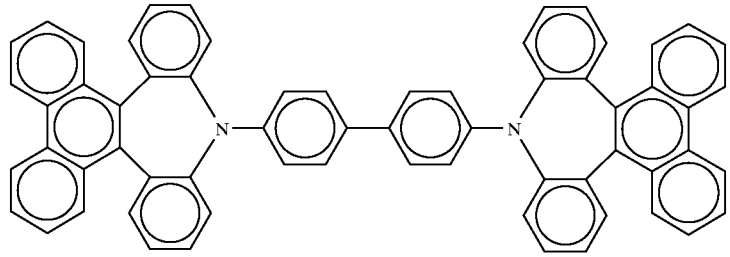

(4)

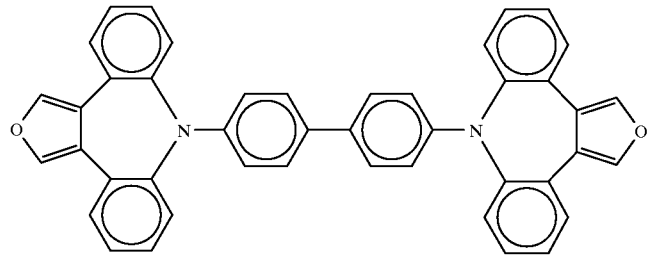

(5)

(6)
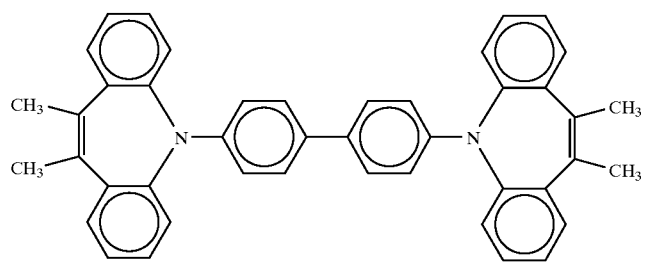
(7)
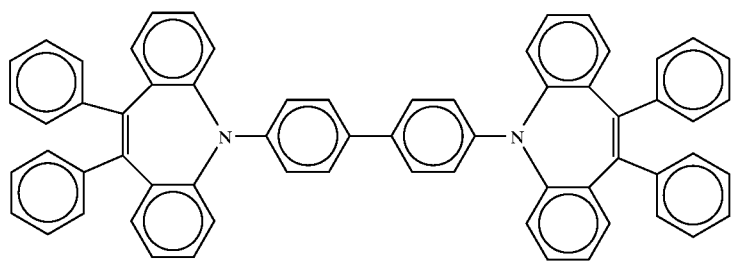
(8)
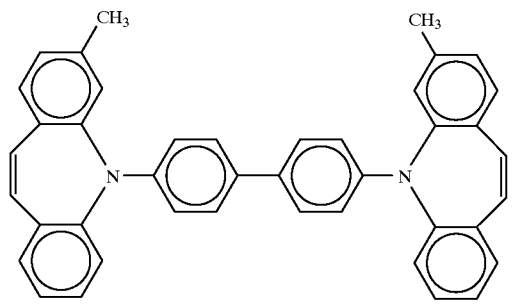
(9)
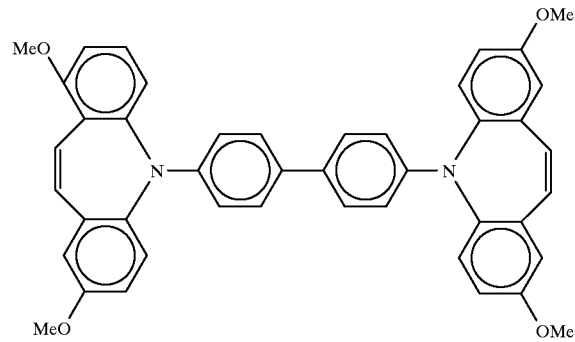
(10)
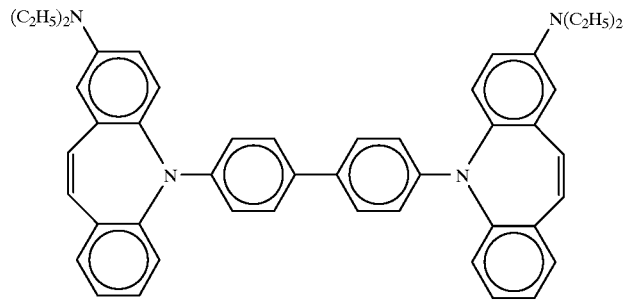

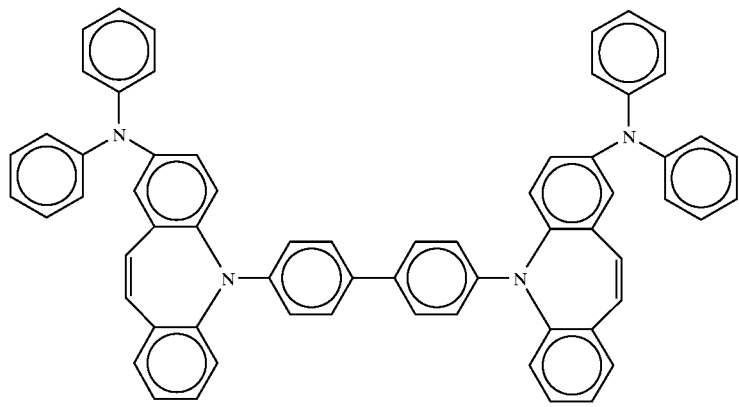
(11)
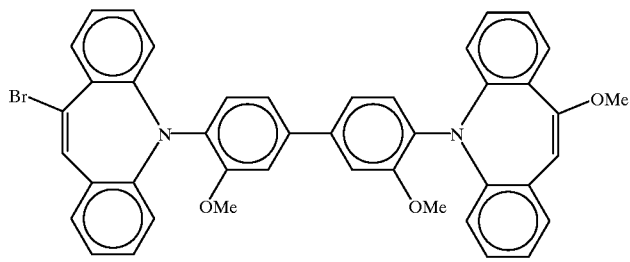
(12)
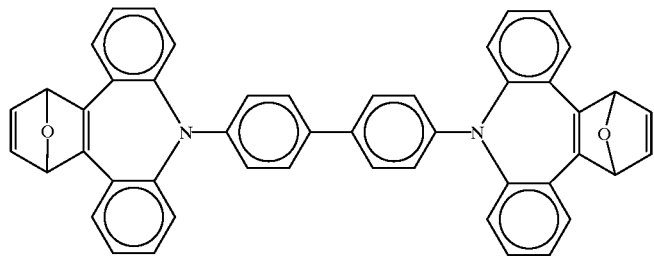
(13)
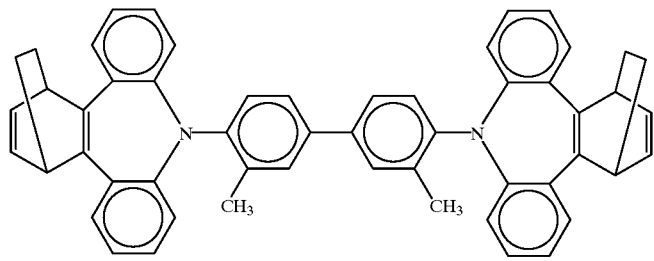
(14)
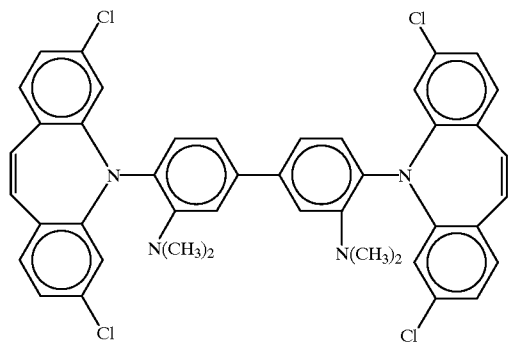
(15)

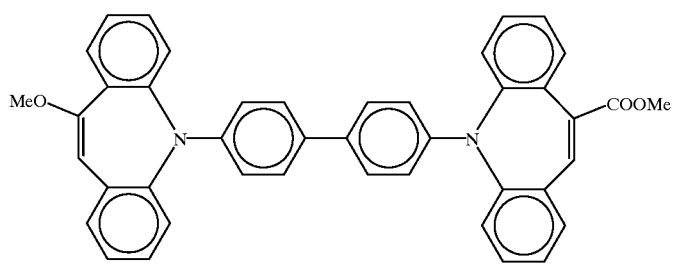
(16)
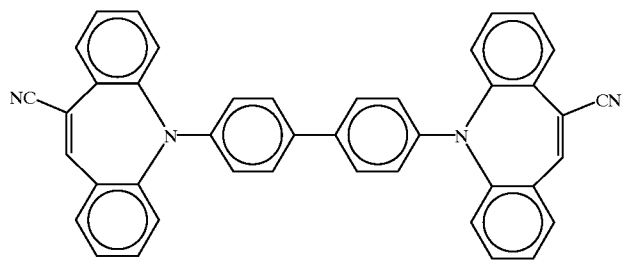
(17)
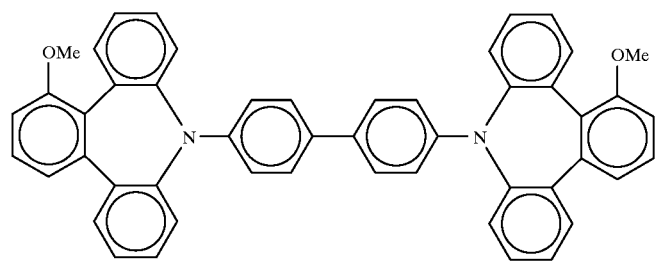
(18)
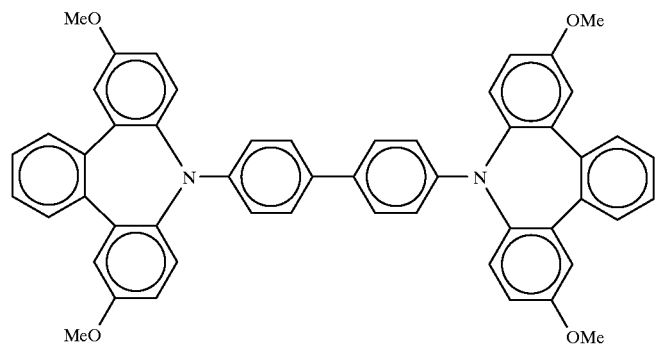
(19)
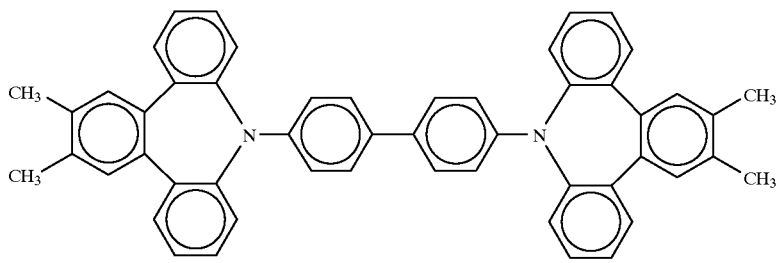
(20)

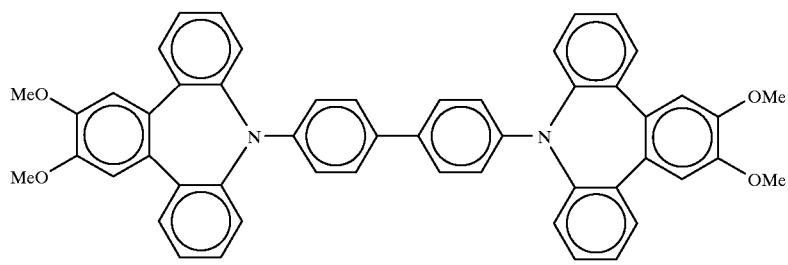
(21)
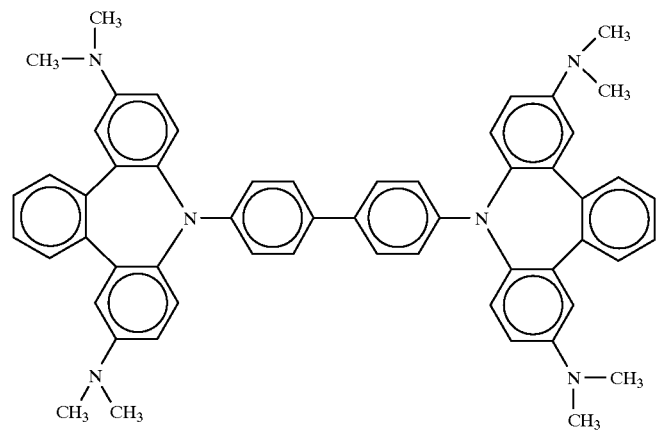
(22)
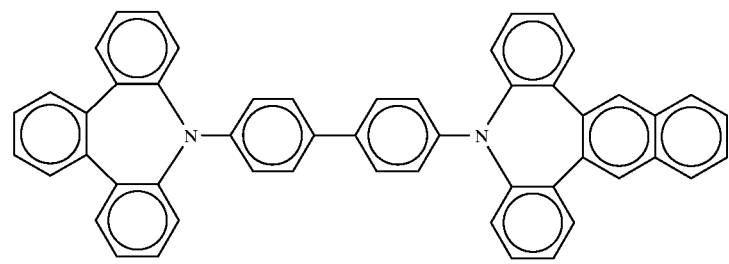
(23)
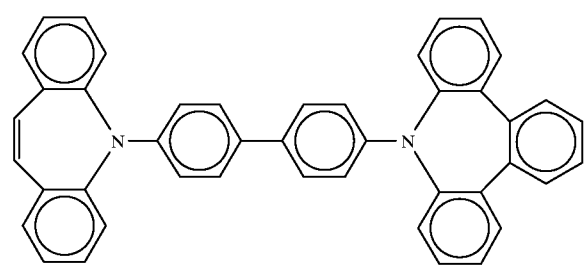
(24)
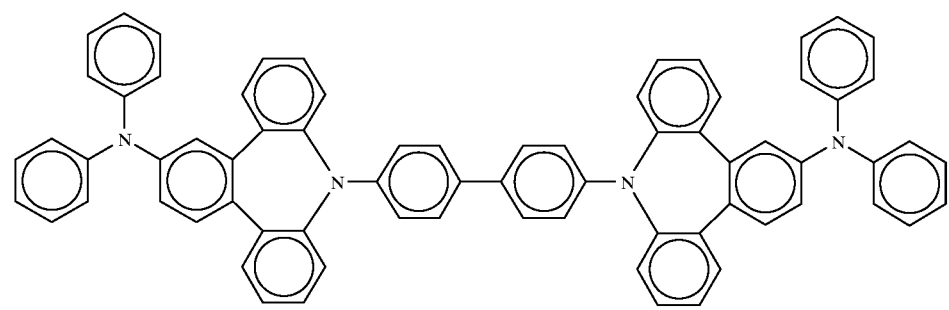
(24)

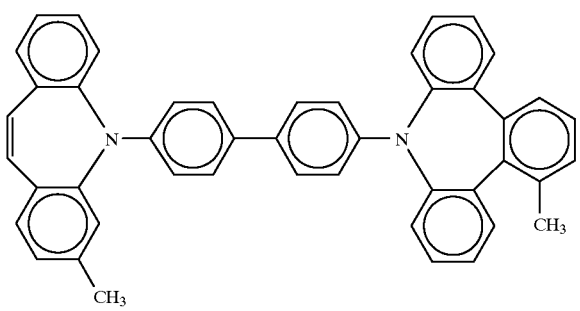
(25)
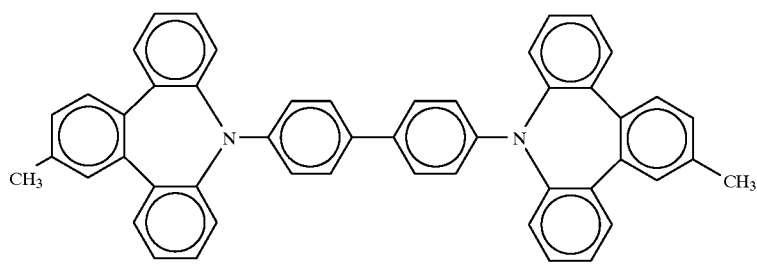
(26)
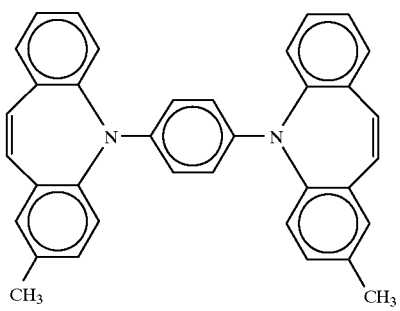
(27)
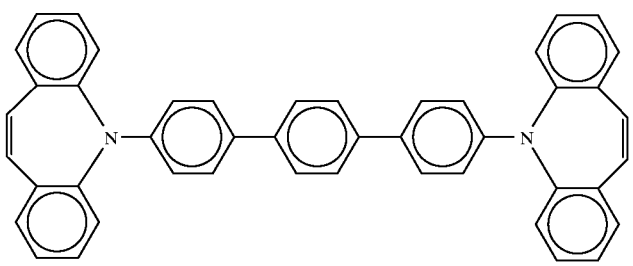
(28)
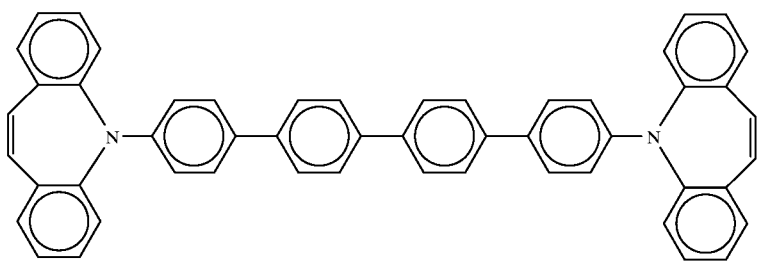
(29)

(30)
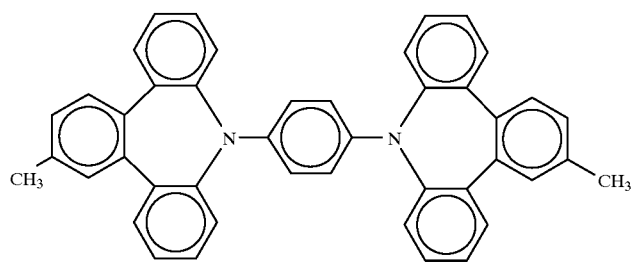
(31)
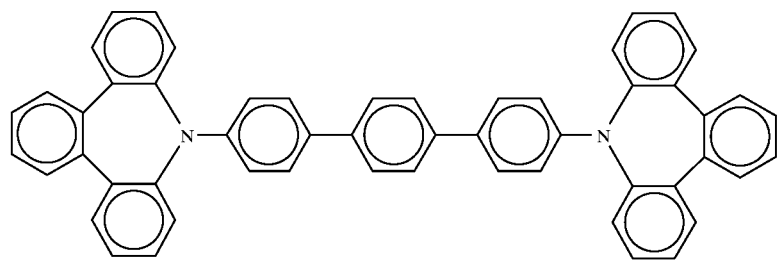
(32)
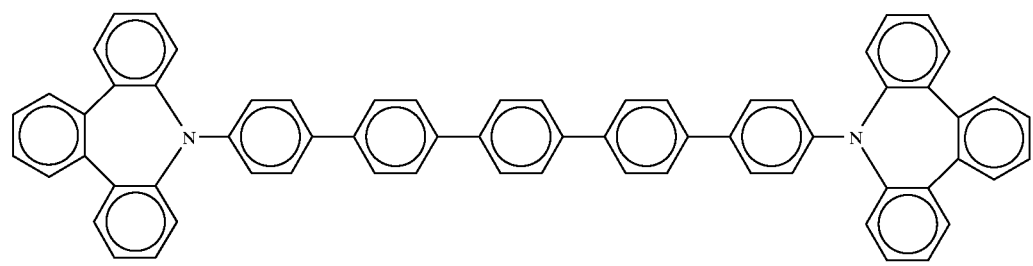
(33)
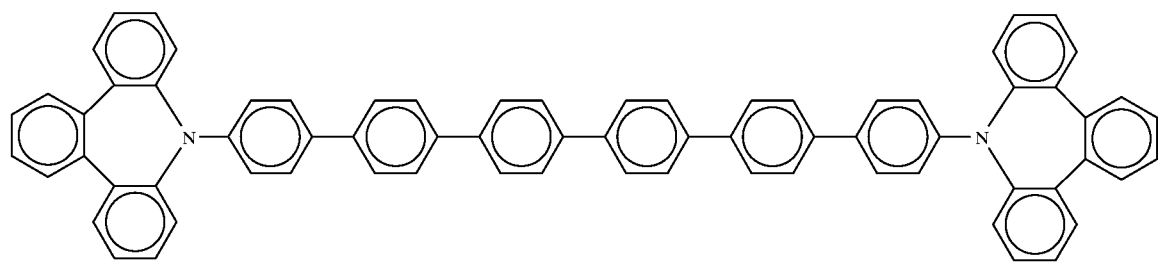
(34)
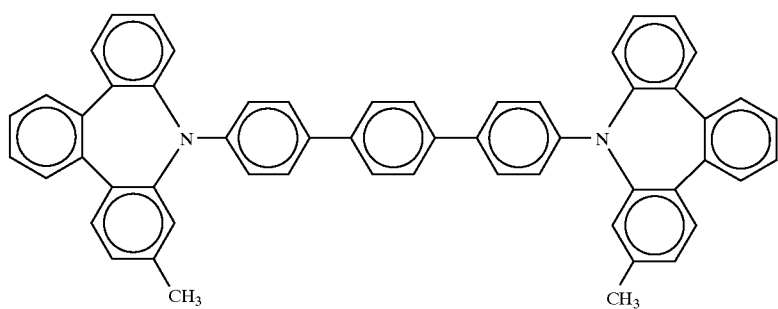

(35)

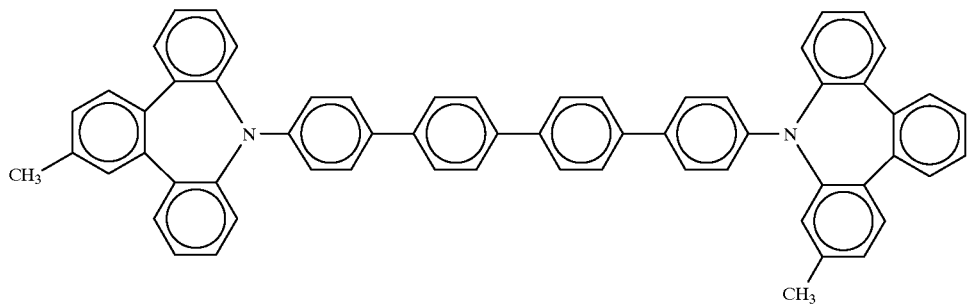

The compounds according to the present invention can be synthesized using any of the typical synthesis methods illustrated below as <Reaction Scheme 1>, <Reaction Scheme 2> and <Reaction Scheme 3> respectively. The synthesis method illustrated as <Reaction Scheme 1> is based on Ullmann reaction using a metallic copper catalyst and a base (For this reaction, U.S. Pat. No. 4,764,625 can be referred to.); while the synthesis methods illustrated as <Reaction Scheme 2> and <Reaction Scheme 3> are based on the cross-coupling reaction using a nickel or palladium metallic catalyst (For this reaction, a book entitled "Dai 4-pan Jikken Kagaku Koza" (which means "The 4th Edition Lectures on Experimental Chemistry"), vol. 25, p. 389 (1991), compiled by Japanese Chemical Society and published by Maruzen).

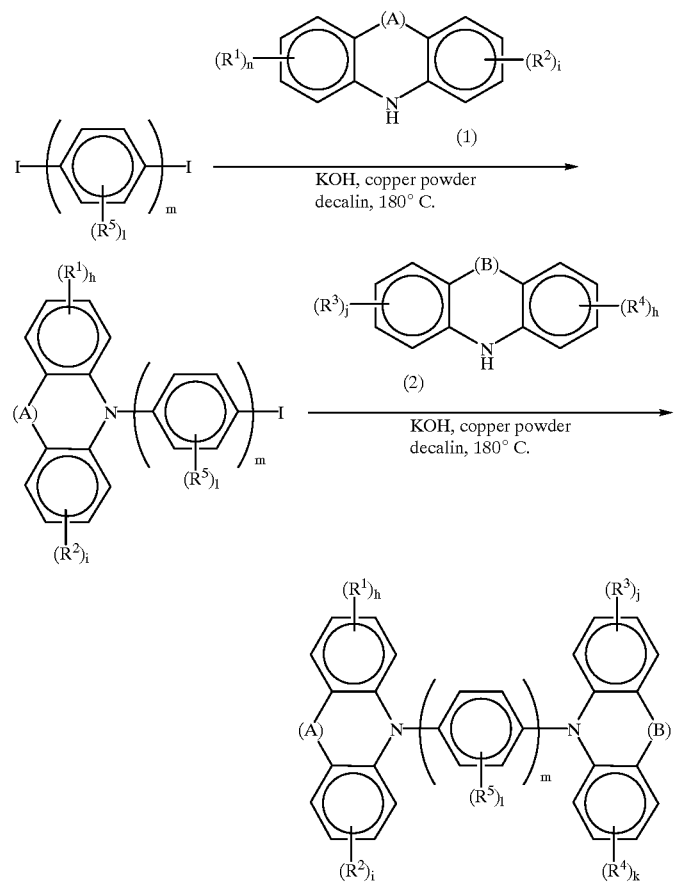

In the above formulae, (A), (B), $R^1$ to $R^5$, and h to m have the same meanings as those described above respectively.

Reaction Scheme 2

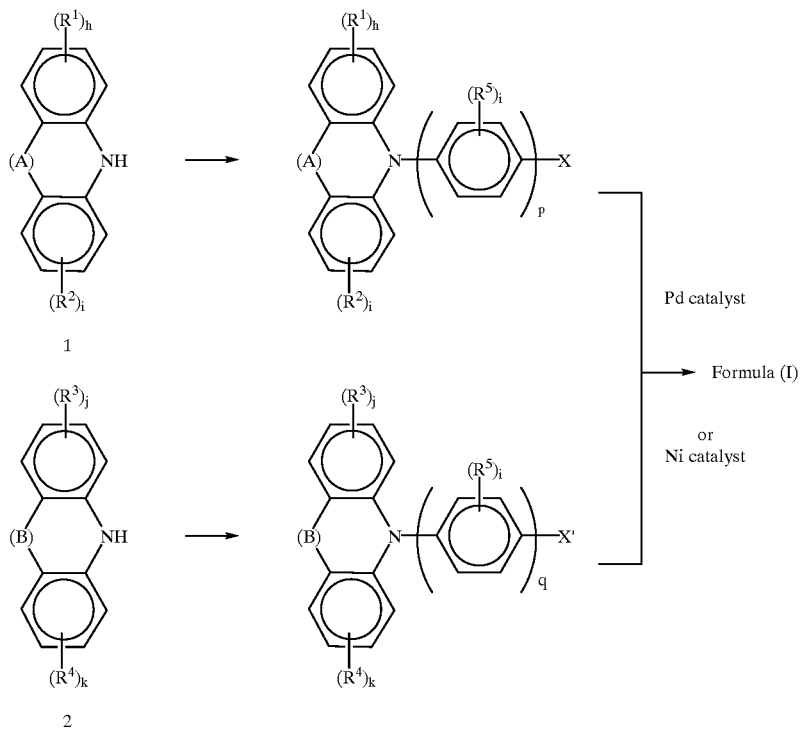

In the above formulae, (A), (B), $R^1$ to $R^5$, and h to l have the same meanings as those described above respectively. X and X' are each a chlorine, bromine or iodine atom, —B(OH)$_z$ or Sn(n-Bu)$_4$, but as far as one of them is a chlorine, bromine or iodine atom, the other is —B(OH)$_z$ or Sn(n-Bu)$_4$.

Reaction Scheme 3

[Synthesis of Compound corresponding to (A) = (B), $(R^1)_h = (R^3)_j$, $(R^2)i = (R^4)_k$ and $1 = 0$ in formula (I)]

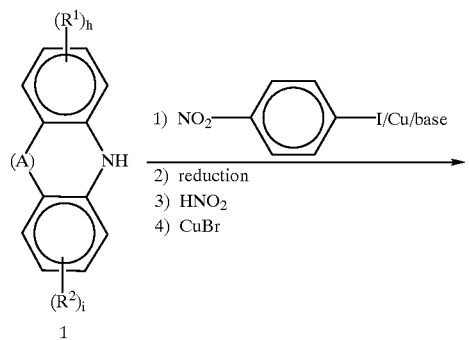

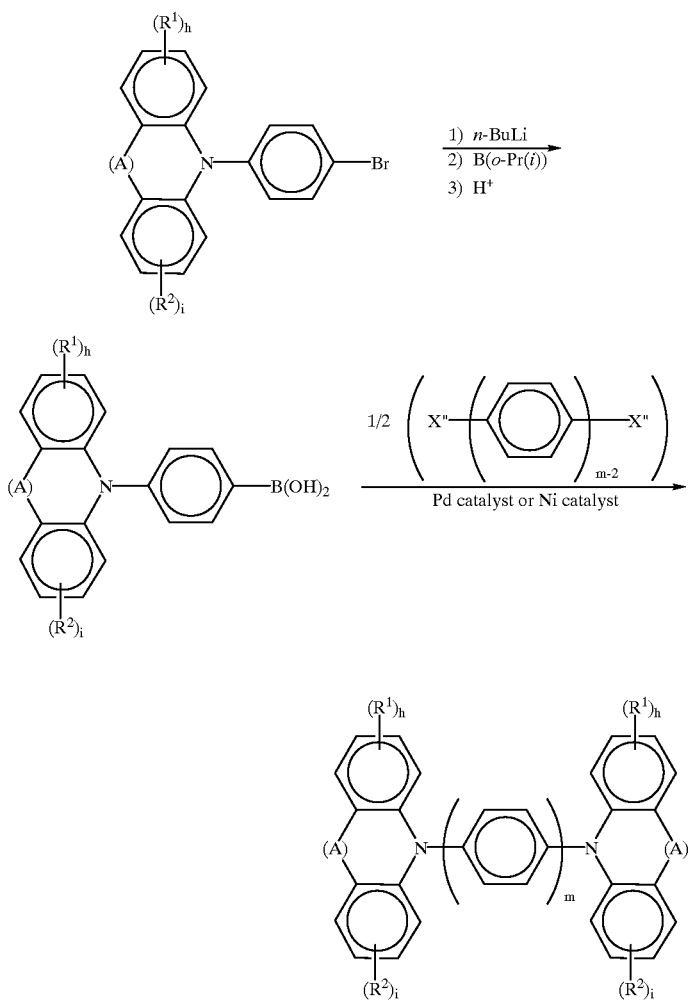

In the above formulae, (A), $R^1$, $R^2$, h, i and m have the same meanings as those described above respectively. X" is a chlorine, bromine or iodine atom.

The benzazepines, (1) and (2), used in the above synthesis methods can be produced according to the methods described in B. Renfroe, C. Harrington, G. R. Proctor, *The Chemistry of Heterocyclic Compounds*, Vol. 43, Part 1, John Wiley & Sons Inc. (1984), and H. C. Axtell et al., *J. Org. Chem.*, 56, 3906 (1991).

The compounds synthesized in accordance with the foregoing reaction schemes can be purified by column chromatography on silica gel and recrystallization, and further sublimation, if needed.

The present invention will now be illustrated in more detail by reference to the following examples. However, the invention should not be construed as being limited to the following examples in any way.

EXAMPLE 1
Synthesis of Exemplified Compound (1)

5H-Dibenz[b,f]azepine in an amount of 17.4 g (90 mmol), 4,4'-diiodobiphenyl in an amount of 12.2 g (30 mmol), potassium hydroxide in an amount of 13.5 g (240 mmol) and a copper powder in an amount of 9.5 g (150 mmol) were mixed with 18 ml of decalin, and heated with stirring in a stream of nitrogen for 28 hours at the external temperature of 200° C. After cooling to room temperature or its vicinity, the reaction solution was admixed with chloroform, and subjected to Celite filtration to remove the insoluble matter. The filtrate was concentrated, and the residue was admixed with n-hexane to remove the decalin. The solid matter was filtered off, and crystallized from methanol. Thus, 8 g of crystals including Exemplified Compound (1) was obtained. These crystals were purified by column chromatography on silica gel (eluent: chloroform+n-hexane), and further recrystallized from methanol to give 2.5 g of Exemplified Compound (1) in a pure form (yield; 15.5%). mp. 288–290° C.

EXAMPLE 2
Synthesis of Exemplified Compound (2)

9H-Tribenz[b,d,f]azepine (synthesized in accordance with the method described in *J. Orq. Chem.*, 56, 3906 (1991)) in an amount of 18.2 g (75 mmol), 4,4'-diiodobiphenyl in an amount of 10.2 g (25 mmol), potassium hydroxide in an amount of 11.2 g (200 mmol) and a copper powder in an amount of 3.2 g (50 mmol) were mixed with 15 ml of decalin, and heated with stirring in a stream of nitrogen for 18 hours at the external temperature of 200° C. After cooling to room temperature or its vicinity, the reaction solution was admixed with chloroform, and subjected to Celite filtration to remove the insoluble matter. The filtrate was concentrated, and the residue was admixed with methanol. Thereto, heat is applied, and thereby a crystalline precipitate was deposited. This crystalline precipitate was filtered off. It was confirmed by thin-layer silica gel chromatography that, besides Exemplified Compound (2), impurities were present in the crystalline precipitate obtained (21 g). Thus, the crystalline precipitate was subjected to the purification using silica gel column chromatography (eluent: chloroform+n-hexane), and further to the recrystallization from a chloroform/n-hexane mixture to give 2.4 g of crystals. However, the purity thereof was insufficient. Therefore, these crystals were purified again by column chromatography and recrystallization. By these-procedures, 1.6 g of Exemplified Compound (2) in a pure form was obtained (in a 10% yield). mp. 329–331° C.

EXAMPLE 3
Synthesis of Exemplified Compound (26)

In the same manner as in Example 2, except that 9H-trisbenz[b,d,f]azepine was replaced by the equimolar amount of 2-methyl-9H-tribenz[b,d,f]azepine (synthesized using 3-methylfuran in place of furan in the method disclosed in *J. Org. Chem.*, 56, 3906 (1991)), 3.0 g of Exemplified Compound (26) in a pure form was obtained (in a 18% yield).

EXAMPLE 4
Synthesis of Exemplified Compound (29)

5H-Dibenz[b,f]azepine in an amount of 20.0 g (0.10 mol), 4,4'-diiodobiphenyl in an amount of 60.9 g (0.15 mol), potassium hydroxide in an amount of 6.7 g (0.12 mol) and a copper powder in an amount of 1.3 g (0.02 mol) were mixed with 20 ml of decalin, and heated with stirring in a stream of nitrogen for 36 hours at the external temperature of 200° C. After cooling to room temperature or its vicinity, the reaction solution was admixed with chloroform, and subjected to Celite filtration to remove the insoluble matter. The filtrate was concentrated, and the concentrated solution was purified by column chromatography on silica gel. Thus, 23.6 g of 5-(4'-iodobiphenyl-4-yl)dibenz[b,f]azepine was obtained (in a 50% yield).

A 10 g portion (0.021 mol) of 5-(4'-iodobiphenyl-4-yl) dibenz[b,f]azepine was dissolved in 50 ml of tetrahydrofuran (THF), and cooled to −78° C. Thereto, 33.6 ml (0.021 mol) of a 1.6M solution of n-butyl lithium in hexane was added dropwise, and then stirred for 30 minutes. Thereafter, a THF solution containing 2.2 g (0.021 mol) of trimethyl borate was further added dropwise over a period of about 1 hour. After one-hour stirring, the temperature of the reaction solution was raised slowly up to room temperature, and the reaction was run for additional 2 hours. Then, the reaction mixture was subjected to hydrolysis by adding thereto dilute sulfuric acid (3 ml of sulfuric acid+50 ml of water) at 0° C., extracted with ethyl acetate, and further concentrated under reduced pressure. The thus obtained solid borate was purified by recrystallization from toluene to give 6.9 g of 4'-(dibenz[b,f]azepine-5-yl)biphenyl-4-yl borate (in a 85% yield).

A mixture of 5 g (0.011 mol) of 5-(4'-iodobiphenyl-4-yl) dibenz[b,f]azepine, 4.3 g (0.011 mol) of 4'-(dibenz[b,f] azepine-5-yl)biphenyl-4-yl borate, 25 mg (0.11 mmol) of palladium acetate, 85 mg (0.28 mmol) of tri-o-tolyl phosphine, 2.2 g (0.022 mol) of triethylamine and 50 ml of N-dimethylformamide was heated for about 2 hours at 100° C. The solvent was distilled away under reduced pressure, and the residue was admixed with chloroform and 10% aqueous ammonia. Then, the mixture was subjected to an extraction procedure, dried over anhydrous magnesium sulfate, filtered, and concentrated under reduced pressure. The residue thus obtained was recrystallized from a THF-methanol mixture to give 4.9 g of Exemplified Compound (29) (in a 70% yield).

EXAMPLE 5
Synthesis of Exemplified Compound (33)

In almost the same manner as in Example 4, except that 5H-dibenz[b,f]azepine was replaced by the equimolar amount of 9H-tribenz[b,d,f]azepine, 23.5 g of 9-(4'-iodobiphenyl-4-yl)tribenz[b,d,f]azepine was obtained (in a 45% yield).

In the next place,, 4'-(tribenz[b,d,f]azepine-9-yl)biphenyl-4-yl borate was obtained in an amount of 7.4 g (yield: 80%) in almost the same manner as in Example 4, except that 5-(4'-iodobiphenyl-4-yl)dibenz[b,f]azepine was replaced by the equimolar amount of 9-(4'-iodobiphenyl-4-yl)tribenz[b, d,f]azepine.

A mixture of 5.0 g (0.011 mol) of 4'-(tribenz[b,d,f] azepine-9-yl)biphenyl-4-yl borate, 2.3 g (0.0057 mol) of 4,4'-diiodobiphenyl, 13 mg (0.057 mmol) of palladium acetate, 43 mg (0.14 mmol) of tri-o-tolyl phosphine, 1.2 g (0.011 mol) of triethylamine and 50 ml of N-dimethylformamide was heated for about 4 hours at 100° C. reaction mixture underwent the same after-treatment as in Example 4, and further the same purification procedure as in Example 4 to give 3.5 g of Exemplified Compound (33) (in a 65% yield).

A novel aromatic tertiary amine compound according to the present invention, wherein two benzazepine structures per molecule are present, can be formed into a thin amorphous film, which is stable at ordinary temperature, by means of a vacuum evaporation technique and, what is more, the thin film made of the compound by itself can have a large area. Moreover, the present compound has a high glass transition temperature, and the amorphous film thereof has excellent thermal resistance and, in other words, high stability. Thus, it becomes possible to design an organic electroluminescent device which can withstand the light emission for a longer time than usual, namely have a longer lifetime, by using the present compound formed into a thin film as a material for the hole transporting layer of an organic electroluminescent device. Further, the present compound can function effectively as a carrier transporting material for electrophotography, so that it enables a great improvement in electrophotographic performance.

What is claimed is:

1. An aromatic tertiary amine compound represented by formula (I):

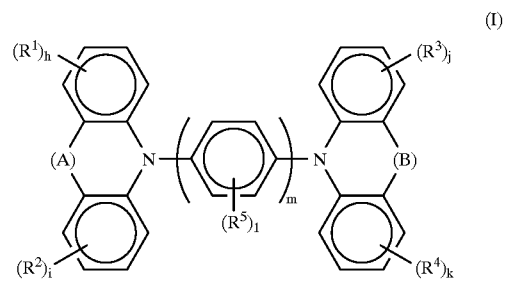

wherein (A) and (B) are each a substituted or unsubstituted vinylene or o-arylene group; $R^1$, $R^2$, $R^3$ and $R^4$ are each a halogen atom, or a substituted or unsubstituted alkyl, aryl, alkoxy, aryloxy, dialkylamino, N-alkyl-N-arylamino or diarylamino group; $R^5$ is a halogen atom, or a substituted or unsubstituted alkyl, alkoxy or dialkylamino group; h, i, j, k and l are each an integer of from 0 to 4; m is an integer of from 1 to 6; and wherein, when m is 2 or more, $(R^5)_l$ present on the respective benzene rings are the same as or different from one another.

2. An aromatic tertiary amine compound represented by formula (II):

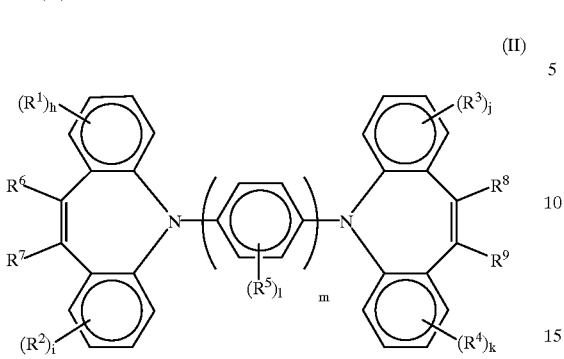

wherein $R^1$, $R^2$, $R^3$ and $R^4$ are each a halogen atom, or a substituted or unsubstituted alkyl, aryl, alkoxy, aryloxy, dialkylamino, N-alkyl-N-arylamino or diarylamino group; $R^5$ is a halogen atom, or a substituted or unsubstituted alkyl, alkoxy or dialkylamino group; h, i, j, k and l are each an integer of from 0 to 4; m is an integer of from 1 to 6; when m is 2 or more, $(R^5)_l$ present on the respective benzene rings are the same as or different from one another; and $R^6$, $R^7$, $R^8$ and $R^9$ are each a hydrogen atom, a substituted or unsubstituted alkyl, aryl, alkoxy or alkoxycarbonyl group, or a cyano group.

3. An aromatic tertiary amine compound represented by formula (III)

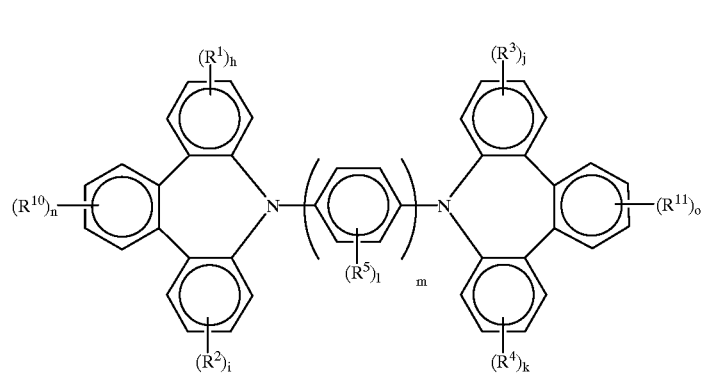

wherein $R^1$, $R^2$, $R^3$, $R^4$, $R^{10}$, and $R^{11}$ are each a halogen atom, or a substituted or unsubstituted alkyl, aryl, alkoxy, aryloxy, dialkylamino, N-alkyl-N-arylamino or diarylamino group; $R^5$ is a halogen atom, or a substituted or unsubstituted alkyl, alkoxy or dialkylamino group; h, i, j, k, l, n and o are each an integer of from 0 to 4; m is an integer of from 1 to 6; when m is 2 or more, $(R^5)_l$ present on the respective benzene rings are the same as or different from one another.

4. An aromatic tertiary amine compound as claimed in claim 1, wherein the vinylene and o-arylene groups represented by (A) and (B) are the following groups:

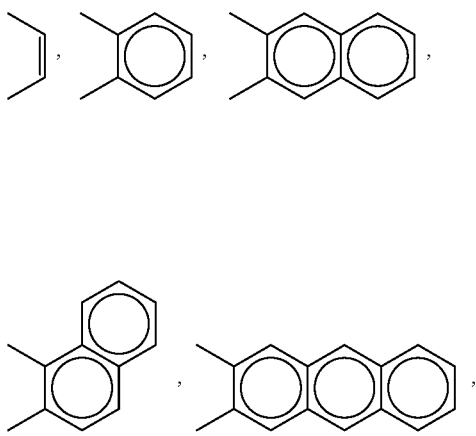

-continued

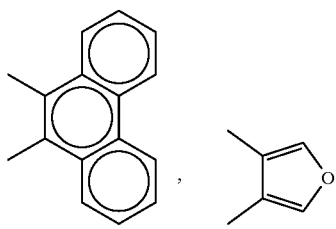

* * * * *